United States Patent [19]

Shimomura et al.

[11] Patent Number: 5,905,160
[45] Date of Patent: May 18, 1999

[54] METHOD FOR PRODUCTION OF EPOXY COMPOUND AND HYDROXY IMINODISUCCINIC ACID

[75] Inventors: Masatoshi Shimomura; Miaki Asakawa; Yuichi Kita, all of Hyogo, Japan

[73] Assignee: Nippon Shokubai Co., Ltd., Osaka-fu, Japan

[21] Appl. No.: 08/741,375

[22] Filed: Oct. 30, 1996

[30] Foreign Application Priority Data

Oct. 31, 1995 [JP] Japan .................................. 7-283270

[51] Int. Cl.⁶ .................................................. C07D 301/12
[52] U.S. Cl. ........................................... 549/531; 562/567
[58] Field of Search ............................... 549/531; 562/567

[56] References Cited

U.S. PATENT DOCUMENTS

| | | |
|---|---|---|
| 3,518,285 | 6/1970 | Fenton et al. . |
| 4,028,407 | 6/1977 | Petritsch et al. . |
| 5,274,140 | 12/1993 | Venturello et al. ...................... 549/531 |
| 5,318,726 | 6/1994 | Rossmaier et al. ...................... 252/546 |
| 5,430,161 | 7/1995 | Brown et al. ........................... 549/531 |

FOREIGN PATENT DOCUMENTS

| | | |
|---|---|---|
| 0074259 | 9/1982 | European Pat. Off. . |
| 0568336 | 4/1993 | European Pat. Off. . |

OTHER PUBLICATIONS

European Search Report, EP 96 30 7829, Feb. 21, 1997.

*Primary Examiner*—Ba K. Trinh
*Attorney, Agent, or Firm*—Omri M. Behr, Esq.

[57] ABSTRACT

The epoxidation is carried out in a reaction system made of metal under conditions such that the inner surface area (S) of the reaction system exposed to the gaseous-phase part thereof and the amount of the reaction solution (V) in the reaction system satisfy the formula: $0<S/V\leq 2$ $(m^2/m^3)$. The epoxidation, otherwise, is carried out in a reaction vessel such that at least the inner surface thereof exposed to the gaseous-phase part thereof has been inactivated or in a reaction vessel such that at least the inner surface thereof exposed to the gaseous-phase part thereof has been inactivated. A hydroxy iminodisuccinic acid is produced by causing the epoxysuccinic acid which has been obtained as described above to react with L-aspartic acid. By this reaction, an epoxy compound can be produced with a high yield without inducing coloration by epoxidizing a corresponding ethylenic compound with hydrogen peroxide. By using the epoxysuccinic acid obtained as described above, hydroxy iminodisuccinic acid of high quality can be produced without inducing coloration.

8 Claims, No Drawings

1

METHOD FOR PRODUCTION OF EPOXY COMPOUND AND HYDROXY IMINODISUCCINIC ACID

BACKGROUND OF THE INVENTION

1. Field of the Invention

This invention relates to a method for the production of an epoxy compound. More particularly, this invention relates to a method which comprises epoxidizing an ethylenic compound with hydrogen peroxide thereby producing a corresponding epoxy compound and hydroxy iminodisuccinic acid with a high yield without inducing coloration.

2. Description of the Prior Art

The method for producing an epoxy compound by epoxidizing a corresponding ethylenic compound with hydrogen peroxide has been known for a long time. The catalyst, reaction condition, etc. to be used for this reaction are being studied with great enthusiasm. Numerous patents and documents have already issued from the researches.

As one way of producing epoxysuccinic acid by epoxidizing maleic anhydride with hydrogen peroxide, the present inventors have proposed a method for obtaining epoxysuccinates with a high yield by using two different reaction temperatures and thereby economizing the epoxidizing catalyst (JP-A-04-290879).

No reports have been published concerning the study on the material for the reaction vessel to be used in the epoxidation of maleic anhydride with hydrogen peroxide. The fact that glass, stainless steel, aluminum, etc. are usable as materials for the vessels to be used in handling hydrogen peroxide has been barely known.

The present inventors, in order to produce epoxysuccinic acid on a commercial scale, have tried the epoxidation with a reaction vessel made of stainless steel which is popularly used as an industrial grade material. They have consequently found that this reaction vessel entails the problem of lowering the yield of epoxysuccinic acid relative to maleic anhydride and inducing the produced reaction solution to undergo coloration. After a further study on this problem, they have found that part of hydrogen peroxide gasifies during the course of the reaction, contacts with the surface of stainless steel in the gaseous phase part of the reaction vessel, and undergoes the decomposition caused by the action of stainless steel. Their study has boiled down to a conclusion that when hydrogen peroxide is supplied in an equimolar amount to maleic anhydride, the yield of epoxysuccinic acid relative to maleic anhydride is ultimately lowered because of the decomposition of hydrogen peroxide. Though the cause for the coloration of epoxysuccinic acid has not yet been elucidated, the coloration may be logically explained by a supposition that the decomposition of hydrogen peroxide entrains a secondary reaction of some form or other and the by-product arising from this secondary reaction persists in epoxysuccinic acid and imparts a color thereto.

The lowered yield induces a decrease in productivity and the coloration seriously impairs the salability of the product, both of which prove unfavorable.

This invention, concerning the production of an epoxy compound by the epoxidation of a corresponding ethylenic compound with hydrogen peroxide in a reaction vessel made of a metal, is aimed at solving such problems as the decomposition of hydrogen peroxide which occurs during the course of the reaction and the degradation of yield and the coloration of the epoxy compound which ensue from the decomposition and consequently enabling the epoxy compound to be produced with a high yield without inducing coloration.

Further, this invention is aimed at producing hydroxy iminodisuccinic acid of high quality without inducing coloration.

SUMMARY OF THE INVENTION

The inventors have found as a result of their study that when the reaction of epoxidation is performed in a reaction vessel made of a metal, the problem mentioned above can be solved by either adjusting the ratio of the inner surface area of the reaction system exposed to the gaseous-phase part of the reaction system to the amount of the reaction solution in the reaction vessel within a specific range or inactivating the inner surface of the reaction system exposed to the gaseous-phase part of the reaction system. This invention has been perfected based on this knowledge.

Specifically, this invention concerns a method for the production of an epoxy compound by the epoxidation of a corresponding ethylenic compound with hydrogen peroxide, which method is characterized in that the epoxidation is carried out in a reaction system made of a metal under conditions such that the inner surface area (S: $m^2$) of the reaction system exposed to the gaseous-phase part of the reaction system and the amount of the reaction solution (V: $m^3$) in the reaction system satisfy the formula: $0<S/V\leq 2$ ($m^2/m^3$).

This invention also concerns a method for the production of an epoxy compound by the epoxidation of a corresponding ethylenic compound with hydrogen peroxide, which method is characterized in that the epoxidation is carried out in a reaction system such that at least the inner surface thereof exposed to the gaseous-phase part thereof has been inactivated.

This invention further concerns a method for the production of an epoxy compound by the epoxidation of a corresponding ethylenic compound with hydrogen peroxide, which method is characterized in that the epoxidation is carried out in a reaction vessel such that at least the inner surface thereof exposed to the gaseous-phase part thereof has been inactivated.

This invention further concerns a method for the production of hydroxy iminodisuccinic acid, characterized in that the production is effected by causing epoxysuccinic acid obtained by the method for the production of an epoxy compound mentioned above to react with L-aspartic acid.

DESCRIPTION OF PREFERRED EMBODIMENT

The term "reaction system" as used in this invention refers collectively to a reaction vessel and pipes, valves, etc. which are provided in the reaction vessel and the expression "the inner surface area of the reaction system exposed to the gaseous-phase part of the reaction system" mentioned above means the total of inner surface areas of the reaction vessel, pipes, valves, etc. which are exposed to the gaseous-phase part. The inner surface areas of the pipes, valves, etc. as well as the inner surface area of the reaction vessel can be easily calculated based on their diameters and lengths.

As the "reaction vessel made of a metal" to be used in this invention, a reaction vessel made of stainless steel can be advantageously used. As typical examples of the reaction vessel made of a metal to be used in this invention, therefore, reaction vessels which are made of such species of stainless steel as SUS 304, 304L, 316, and 316 L may be cited.

As typical examples of the ethylenic compound to be used in this invention, maleic acid, itaconic acid, acrylic acid, methacrylic acid, crotonic acid, citraconic acid, 2-pentenoic acid, 2-hexenoic acid, 3,4,5,6-tetrahydrophthalic acid, and 3,4,5,6-tetrahydrobenzoic acid, and alkali metal salts (particularly sodium or potassium salts) thereof may be cited. In the case of compounds which are capable of being in an anhydride form such as maleic acid, citraconic acid, etc., the anhydrides of such acids are also embraced.

In these ethylenic compounds, the compounds which are represented by the following general formula (1):

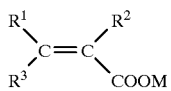

(wherein M stands for a hydrogen atom or an alkali metal and $R^1$, $R^2$, and $R^3$, which may be either identical or different, independently stand for a hydrogen atom, a methyl group, or a group represented by $-(CH_2)_n-COOM$ (wherein M stands for a hydrogen atom or an alkali metal and n is an integer of 0 or 1) and, in the case of compounds capable of forming anhydrides, the anhydrides thereof may be used advantageously. As typical examples of the ethylenic compound represented by the general formula (1), maleic acid, itaconic acid, acrylic acid, methacrylic acid, crotonic acid, and citraconic acid, alkali metal (particularly sodium or potassium) salts thereof, and maleic anhydride and citraconic anhydride may be cited. The method of this invention may be particularly advantageously applied to the production of epoxysuccinic acid by the epoxidization of maleic anhydride.

According to the method of this invention for the production of an epoxy compound by the epoxidation of a corresponding ethylenic compound with hydrogen peroxide in the reaction system made of a metal mentioned above, the reaction of epoxidation is required to be carried out under conditions such that the inner surface area (S: $m^2$) of the reaction system exposed to the gaseous-phase part of the reaction system and the amount of the reaction solution (V: $m^3$) in the reaction system satisfy the formula: $0<S/V\leq 2$ ($m^2/m^3$). So far as this requirement is satisfied, the method and the conditions to be used in carrying out the epoxidation of the ethylenic compound do not need to be particularly limited but may be selected from those commonly used for the reactions of this class.

Now, the method for producing epoxysuccinic acid by the epoxidation of maleic anhydride will be described by way of example. First, the reaction vessel made of a metal mentioned above is charged with maleic anhydride in the form of an aqueous solution in conjunction with an alkali compound and tungstic acid (or salt thereof) and/or molybdic acid (or a salt thereof) as a catalyst. The alkali compound is used for the purpose of adjusting the pH value of the reaction solution in an approximate range of 4 to 6. By adjusting the pH value of the reaction solution within this range, the epoxidation can be carried out highly efficiently. Among other alkali compounds, sodium hydroxide is used particularly advantageously. Then, the aqueous maleic anhydride solution is heated to a temperature in the approximate range of 60° to 90° C. Thereafter, hydrogen peroxide is drip-fed to the hot aqueous maleic anhydride solution to induce the epoxidation of maleic anhydride. This hydrogen peroxide is used generally at a concentration in the approximate range of 30 to 70% by weight in the form of an aqueous solution. In this case, the epoxysuccinic acid is obtained in the form of a sodium salt. The epoxidation in accordance with this invention may be performed either in the form of one-step reaction or in the form of such a two-step reaction as is disclosed in JP-A-04-290879, namely the reaction which consists of a first step carried out at a temperature in the range of 60° to 80° C. and a second step carried out at a temperature at least 5° C. higher than the temperature of the first step.

Since the epoxidation of maleic anhydride is normally effected by charging the reaction vessel with maleic anhydride, a reaction medium (such as water), a catalyst, etc. and then gradually introducing or drip-feeding hydrogen peroxide thereto, the ratio of the aforementioned formula S/V slightly varies along with the course of the reaction. According to the method of this invention, the epoxidation is carried out under conditions such that the ratio may fall in the range of $0<S/V\leq 2$, preferably $0<S/V\leq 1.5$, more preferably $0<S/V\leq 1$ ($m^2/m^3$), throughout the entire course of the reaction. The conditions can be easily realized by first calculating the inner surface area of the reaction system such as the reaction vessel and then adjusting the amounts of the reaction medium, maleic anhydride, and hydrogen peroxide to be used. If the ratio S/V exceeds 2, then hydrogen peroxide will be decomposed so conspicuously as to lower the yield and induce coloration of the product.

According to another method of this invention for the production of an epoxy compound by the epoxidation of a corresponding ethylenic compound with hydrogen peroxide, the epoxidation is carried out in a reaction system in which at least the inner surface of the reaction system exposed to the gaseous-phase part of the reaction system has been inactivated. The term "inactivation" as used herein means deprivation of metallicity. As typical examples of inactivation, vitrification and resinification maybe cited. As concrete examples of the reaction vessel which can be used in implementing this method, not only glass vessels but also metallic vessels in which at least the inner surfaces exposed to the gaseous-phase parts thereof have been lined with glass, resin, or coated with ceramic substance may be cited.

For the purpose of carrying out the epoxidation in the reaction system having inactivated the inner surface thereof exposed to the gaseous-phase part thereof, it suffices to use as the reaction vessel a glass vessel or a metallic vessel having inactivated at least the inner surface thereof exposed to the gaseous-phase part thereof, with the inner surfaces of pipes, valves, etc. exposed to the gaseous-phase part inactivated by being lined with glass, resin, or coated with ceramic substance.

According to yet another method of this invention for the production of an epoxy compound by the epoxidation of a corresponding ethylenic compound with hydrogen peroxide, the epoxidation is carried out in a reaction vessel having inactivated at least the inner surface thereof exposed to the gaseous-phase part thereof. The term "inactivation" as used herein has the same meaning as defined above. As concrete examples of the reaction vessel which can be used in implementing this method, therefore, not only glass vessels but also metallic vessels in which at least the inner surfaces exposed to the gaseous-phase parts thereof have been lined with glass, resin, or coated with ceramic substance may be cited.

This invention further provides a method for the production of hydroxy iminodisuccinic acid by the reaction of L-aspartic acid with epoxysuccinic acid which is obtained by the method of this invention for the production of an epoxy compound mentioned above. The molar ratio of epoxysuccinic acid to L-aspartic acid in the reaction mentioned above is appropriate in the range of 1.05:1 to 1:1.05. This reaction is appropriately carried out wholly or predominantly in an aqueous solvent. The solvents other than water which are usable effectively in the reaction include alcohols such as methanol and ethanol and dioxane, for example. The reaction is generally carried out in a neutral to alkaline state which is attained by the addition of the aqueous solution of an alkali hydroxide or ammonium hydroxide.

To be specific, an aqueous solution having L-aspartic acid contained therein at a concentration in the range of 20 to 30% by weight, about 2 moles of an alkali hydroxide, preferably sodium hydroxide, added thereto, and about 1 mole of a dialkali salt, preferably disodium salt, of epoxysuccinic acid added subsequently thereto are together stirred until the reaction of these reactants is completed. The duration of this reaction is in the range of 1 to 8 hours. To promote this reaction, the reaction temperature may be kept in the range of 80° to 100° C. The reaction solution resulting from the reaction is distilled by the use of a rotary evaporator, for example, to expel the solvent and obtain a colorless solid tetraalkali salt of 3-hydroxy-2-2'-iminodisuccinic acid substantially quantitatively. From this crude product or the solvent-containing crude product, free 3-hydroxy-2-2'-iminodisuccinic acid may be obtained by the standard method, namely by the addition of an acid such as hydrochloric acid or sulfuric acid to the product.

Now, this invention will be described more specifically below with reference to working examples.

EXAMPLE 1

In a four-neck flask made of glass and having an inner volume of 1 liter, a test piece of SUS 316 L, 4.5 cm$^2$ in surface area, was set in place in the gaseous-phase part of the flask so as to satisfy S/V=1.1 to 0.8 (m$^2$/m$^3$). The reaction vessel thus prepared was used for synthesizing epoxysuccinic acid by the epoxidation of maleic anhydride.

A solution of 98.1 g (1 mole) of maleic anhydride in 365 g of water, 116.7 g (1.4 moles) of an aqueous 48% sodium hydroxide solution, and 0.33 (0.001 mole) of sodium tungstate dihydrate were together stirred and heated to 70° C. The content of the flask formed a substantially homogeneous solution and assumed a pH value of 5.5 when the temperature reached 70° C. To this solution, 56.7 g (1.0 mole) of an aqueous 60% hydrogen peroxide solution was drip-fed to induce a reaction. Since the pH value lowered as the reaction proceeded, the aqueous 48% sodium hydroxide solution was added to the solution so as to control the pH in the range of 4.5 to 5.5 and the solution was kept at 70° C. for 60 minutes. Then, the reaction was continued with the temperature thereof elevated to 80° C. After the elapse of 3 hours following the start of the reaction, the reaction was terminated by equivalently neutralizing the organic acid in the reaction solution with an aqueous 48% sodium hydroxide solution.

The reaction solution at the end of the reaction was colorless and transparent. The yield of disodium epoxysuccinate (based on maleic anhydride) was 92.6 mol %.
Control 1

The epoxidation was performed by repeating the procedure of Example 1 while using a test piece of SUS 316L, 13.5 cm$^2$ in surface area, so as to satisfy S/V=3.3 to 2.3 (m$^2$/m$^3$).

The reaction solution at the end of the reaction was yellow (colored) and transparent. The yield of disodium epoxysuccinate (based on maleic anhydride) was 80.0 mol %.

From the results of Example 1 and Control 1, it is noted that when the epoxidation was carried out in the reaction vessel made of stainless steel under the condition of S/V>2, the yield of the epoxy compound aimed at was lowered and the produced epoxy compound was colored.

EXAMPLE 2

A four-neck flask made of glass and having an inner volume of 1 liter was used for synthesizing epoxysuccinic acid by the epoxidation of maleic anhydride.

A solution of 98.1 g (1 mole) of maleic anhydride in 365 g of water, 116.7 g (1.4 moles) of an aqueous 48% sodium hydroxide solution, and 0.33 (0.001 mole) of sodium tungstate dihydrate were together stirred and heated to 70° C. The content of the flask formed a substantially homogeneous solution and assumed a pH value of 5.5 when the temperature reached 70° C. To this solution, 56.7 g (1.0 mole) of an aqueous 60% hydrogen peroxide solution was drip-fed to induce a reaction. Since the pH value lowered as the reaction proceeded, the aqueous 48% sodium hydroxide solution was added to the solution so as to control the pH in the range of 4.5 to 5.5 and the solution was kept at 70° C. for 60 minutes. Then, the reaction was continued with the temperature thereof elevated to 80° C. After the elapse of 3 hours following the start of the reaction, the reaction was terminated by equivalently neutralizing the organic acid in the reaction solution with an aqueous 48% sodium hydroxide solution.

The reaction solution at the end of the reaction was colorless and transparent. The yield of disodium epoxysuccinate (based on maleic anhydride) was 92.3 mol %.

EXAMPLE 3

A four-neck separable flask having a barrel part (12 cm in inside diameter and 32 cm in height) made of SUS 316L and a lid part made of glass was used for synthesizing epoxysuccinic acid by the epoxidation of maleic anhydride.

A solution of 588.4 g (6.0 moles) of maleic anhydride in 2190 g of water, 700.2 g (8.4 moles) of an aqueous 48% sodium hydroxide solution, and 1.98 (0.006 mole) of sodium tungstate dihydrate were together stirred and heated to 70° C. The content of the flask formed a substantially homogeneous solution and assumed a pH value of 5.5 when the temperature reached 70° C. To this solution, 340.2 g (6.0 moles) of an aqueous 60% hydrogen peroxide solution was drip-fed to induce a reaction. Since the pH value lowered as the reaction proceeded, the aqueous 48% sodium hydroxide solution was added to the solution so as to control the pH in the range of 4.5 to 5.5 and the solution was kept at 70° C. for 60 minutes. Then, the reaction was continued with the temperature thereof elevated to 80° C. After the elapse of 3 hours following the start of the reaction, the reaction was terminated by equivalently neutralizing the organic acid in the reaction solution with an aqueous 48% sodium hydroxide solution. In this while, the S/V varied in the range of 1.5 to 0.3 (m$^2$/m$^3$). The reaction solution at the end of the reaction was colorless and transparent. The yield of disodium epoxysuccinate (based on maleic anhydride) was 91.5 mol %.
Control 2

The same reaction vessel as used in Example 3 was used for synthesizing epoxysuccinic acid from maleic anhydride as follows.

A solution of 559.0 g (5.7 moles) of maleic anhydride in 2081 g of water, 665.2 g (8.0 moles) of an aqueous 48% sodium hydroxide solution, and 1.88 (0.0057 mole) of sodium tungstate dihydrate were together stirred and heated to 70° C. The content of the flask formed a substantially homogeneous solution and assumed a pH value of 5.5 when the temperature reached 70° C. To this solution, 323.2 g (5.7 moles) of an aqueous 60% hydrogen peroxide solution was drip-fed to induce a reaction. Since the pH value lowered as the reaction proceeded, the aqueous 48% sodium hydroxide solution was added to the solution so as to control the pH in the range of 4.5 to 5.5 and the solution was kept at 70° C. for 60 minutes. Then, the reaction was continued with the temperature thereof elevated to 80° C. After the elapse of 3 hours following the start of the reaction, the reaction was terminated by equivalently neutralizing the organic acid in the reaction solution with an aqueous 48% sodium hydroxide solution. In this while, the S/V varied in the range of 3.9 to 2.2 ($m^2/m^3$). The reaction solution at the end of the reaction was yellow (colored) and transparent. The yield of disodium epoxysuccinate (based on maleic anhydride) was 80.3 mol %.

EXAMPLE 4

A solution was obtained by adding 66.6 g (0.5 mole) of L-aspartic acid to 371 g (0.5 mole) of the aqueous disodium epoxysuccinate solution (having disodium epoxysuccinate contained therein at a concentration of 23.7% by weight) synthesized in Example 1. The solution, with the pH value thereof adjusted to 11 with an aqueous 48% sodium hydroxide solution, was kept at 85° C. for six hours to effect the epoxidation. When the solution obtained by this reaction was analyzed by high-performance liquid chromatography, it was found that tetrasodium hydroxy iminodisuccinate was obtained in a yield of 92.7 mol % (based on L-aspartic acid) and in a purity of 89.7% by weight (a concentration to all organic acid salt in the reaction solution) . When the aqueous disodium epoxysuccinate solutions obtained in Example 2 and Example 3 were similarly caused to react with L-aspartic acid, tetrasodium hydroxy iminodisuccinate was produced in the respective yields of 92.8 mol % and 91.9 mol % (based on L-aspartic acid) and in the purities of 89.8% by weight and 88.6% by weight (concentrations to all organic acid salt in the reaction solution).
Control 3

A solution was obtained by adding 66.6 g (0.5 mole) of L-aspartic acid to 429 g (0.5 mole) of the aqueous disodium epoxysuccinate solution (having disodium epoxysuccinate contained therein at a concentration of 20.5% by weight) synthesized in Control 1. The solution, with the pH value thereof adjusted to 11 with an aqueous 48% sodium hydroxide solution, was kept at 85° C. for six hours to effect the epoxidation. The reaction solution at the end of the reaction was deeper yellow that before the reaction. When the solution obtained by this reaction was analyzed by high-performance liquid chromatography, it was found that tetrasodium hydroxy iminodisuccinate was obtained in a yield of 90.1 mol % (based on L-aspartic acid) and in a purity of 80.6% by weight (a concentration to all organic acid salt in the reaction solution).

When the aqueous disodium epoxysuccinate solutions obtained in Control 2 was similarly caused to react with L-aspartic acid, tetrasodium hydroxy iminodisuccinate was produced in the yield of 89.6 mol % (based on L-aspartic acid) and in the purity of 80.4% by weight (a concentration to all organic acid salt in the reaction solution). The reaction solution at the end of the reaction was deeper yellow that before the reaction.

According to this invention, an epoxy compound can be produced with a high yield without inducing coloration by epoxidizing a corresponding ethylenic compound with hydrogen peroxide as described above. Further by the method of this invention, hydroxy iminodisuccinic acid of high quality can be produced without inducing coloration by using the epoxysuccinic acid obtained as described above.

What is claimed is:

1. A method for the production of an epoxy compound by the epoxidation of a corresponding ethylenic compound with hydrogen peroxide, characterized in that said epoxidation is carried out in a reaction system made of a metal under conditions such that the inner surface area (S: $m^2$) of said reaction system exposed to the gaseous-phase part thereof and the amount of the reaction solution (V: $m^3$) in said reaction system satisfy the formula: $0 < S/V \leq 2$ ($m^2/m^3$).

2. A method for the production of an epoxy compound by the epoxidation of a corresponding ethylenic compound with hydrogen peroxide, which comprises carrying out said epoxidation in a reaction system having metal on its inner surface such that the portion of said metal inner surface area ($S^g$: $m^2$) of said reaction system exposed to the gaseous-phase part thereof and the amount of the reaction solution ($V^s$: $m^3$) in said reaction system satisfy the formula: $0 \leq S^g/V^3 \leq 2$ ($m^2/m^3$).

3. The method of claim 2 wherein at least a portion of the inner surface of the reaction system exposed to the gaseous-phase part thereof has been inactivated.

4. The method of claim 1 wherein the metal is stainless steel.

5. A method for the production of hydroxy iminodisuccinic acid, characterized in that said production is effected by causing epoxysuccinic acid obtained by the method for the production of an epoxy compound set forth in claim 4 to react with L-aspartic acid.

6. The method of claim 2 wherein the metal is stainless steel.

7. The method of claim 2 wherein at least a portion of the metallic inner surface of the reaction system exposed to the gaseous phase has been inactivated by lining it with material selected from the group consisting of glass, resin, and ceramic.

8. The method of claim 2 wherein the inner surface of the reaction system exposed to the gaseous-phase part thereof has been inactivated.

* * * * *